United States Patent [19]
Bertwell et al.

[11] Patent Number: 5,358,503
[45] Date of Patent: Oct. 25, 1994

[54] PHOTO-THERMAL THERAPEUTIC DEVICE AND METHOD

[76] Inventors: Dale E. Bertwell, 2100 Dayton, Denver, Colo. 80231; Joseph P. Markham, 12094 W. 75th Pl., Arvad, Colo. 80005

[21] Appl. No.: 187,399

[22] Filed: Jan. 25, 1994

[51] Int. Cl.$^5$ ............................................. A61N 5/06
[52] U.S. Cl. ......................................... 606/27; 606/2; 606/3; 606/9; 607/115; 607/88
[58] Field of Search ...................... 606/2, 3, 9, 27, 10, 606/11, 13; 607/88, 89, 93, 94, 115

[56] References Cited

U.S. PATENT DOCUMENTS

| | | | |
|---|---|---|---|
| 4,622,972 | 11/1986 | Giebeller et al. | 607/88 X |
| 4,653,495 | 3/1987 | Nanaumi | 606/9 X |
| 4,917,084 | 4/1990 | Sinofsky | 607/89 X |
| 5,000,752 | 3/1991 | Hoskin et al. | 607/89 X |
| 5,178,617 | 1/1993 | Kuizenga et al. | 606/9 |
| 5,259,380 | 11/1993 | Mendes et al. | 606/9 X |
| 5,300,097 | 4/1994 | Lerner et al. | 607/93 |

*Primary Examiner*—Peter A. Aschenbrenner
*Attorney, Agent, or Firm*—Fields, Lewis, Pittenger, Rost & Smith

[57] ABSTRACT

An apparatus, for simultaneous or selective treatment of an area of the skin and adjacent subcutaneous structure of a patient utilizing photo energy and therapeutic heat, which includes a plurality of juxtaposed diodes. Each diode has a longitudinal axis and is capable of projecting a non-coherent cone of light which overlaps the cone of light from each juxtaposed diode so that the light completely covers the treatment area. A flexible pad or appliance holds the diodes in juxtaposed position with each other. Each is held in contact with the skin and has a longitudinal axis which is in substantially perpendicular relationship to the skin. A resistor heats each diode, which acts as a heat sink, so that the treatment area of the skin and the adjacent subcutaneous structure of the mammal receive light and thermal treatment simultaneously. An adjustable control varies the light intensity of the diodes and the amount of heat generated by the resistor in a selected and controlled manner. Indicia is provided for visibly indicating the setting of the control means so that repetitive treatment is possible. A grid system can be established over at least a portion of the surface of the skin of a population of patients to establish a data base for establishing treatment parameters for future patients.

23 Claims, 5 Drawing Sheets

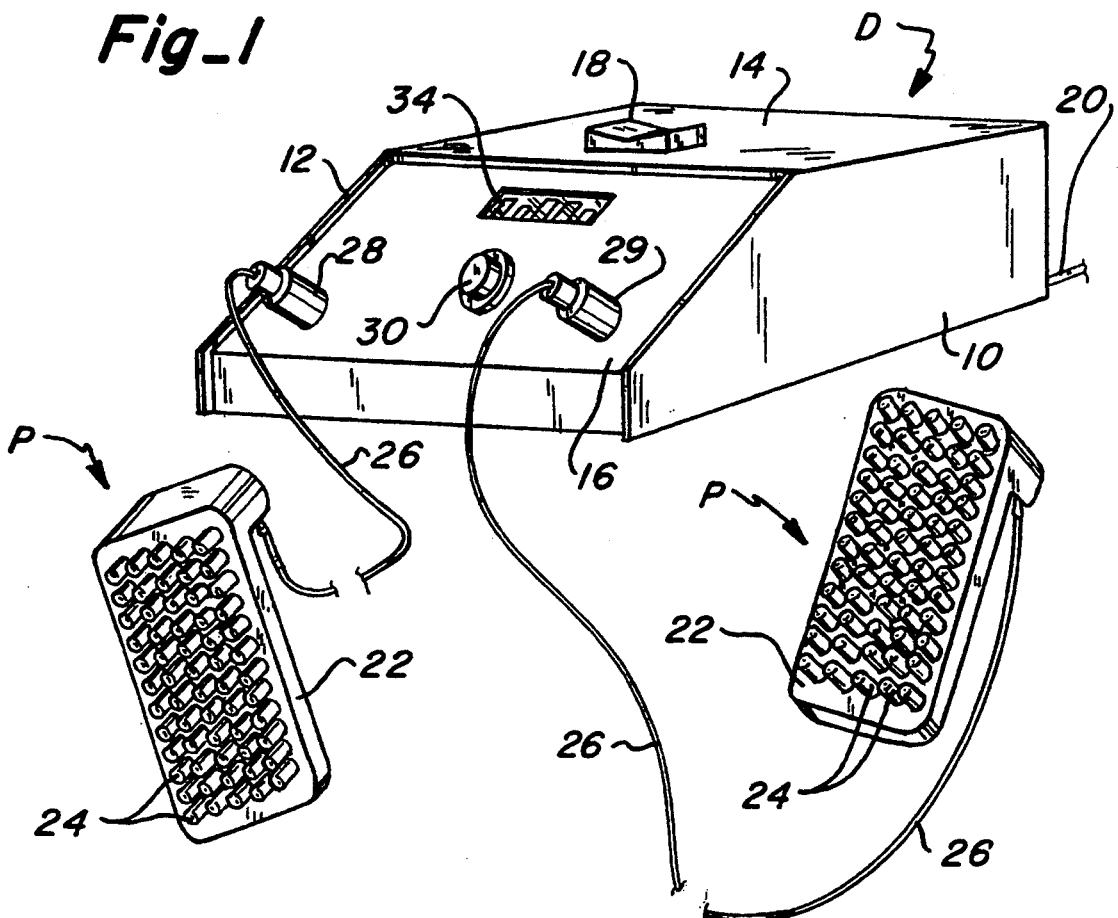
Fig_1
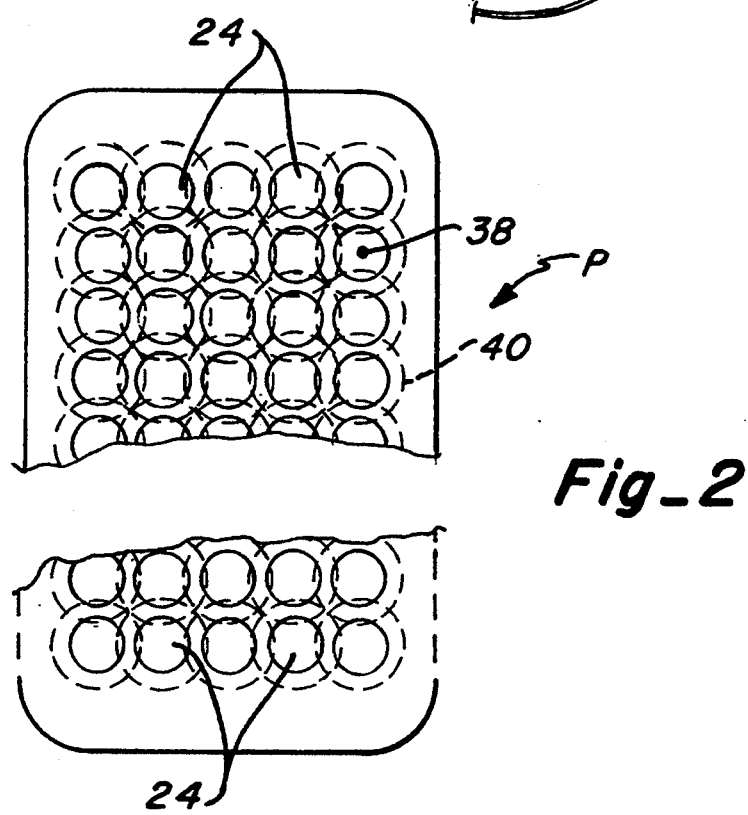
Fig_2

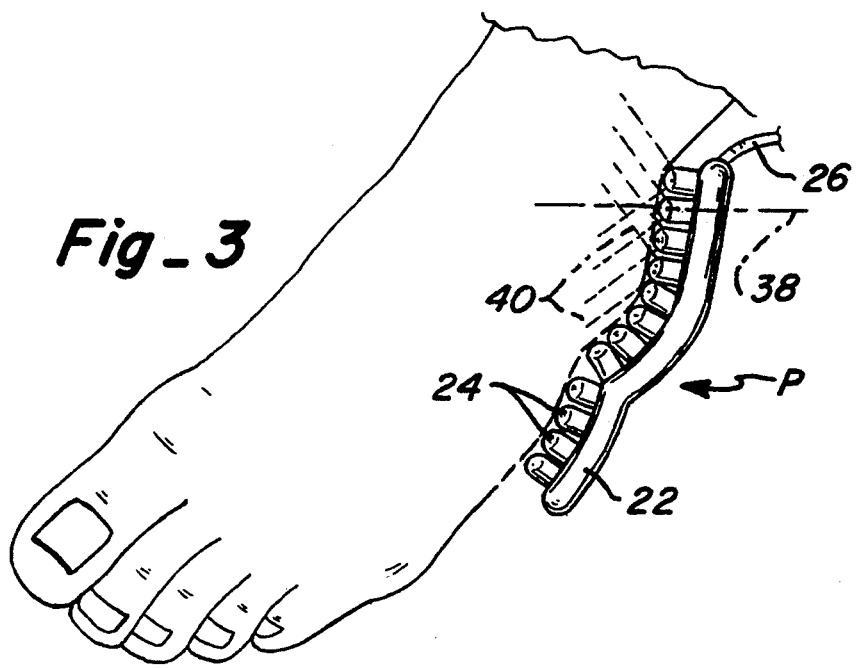
Fig_3
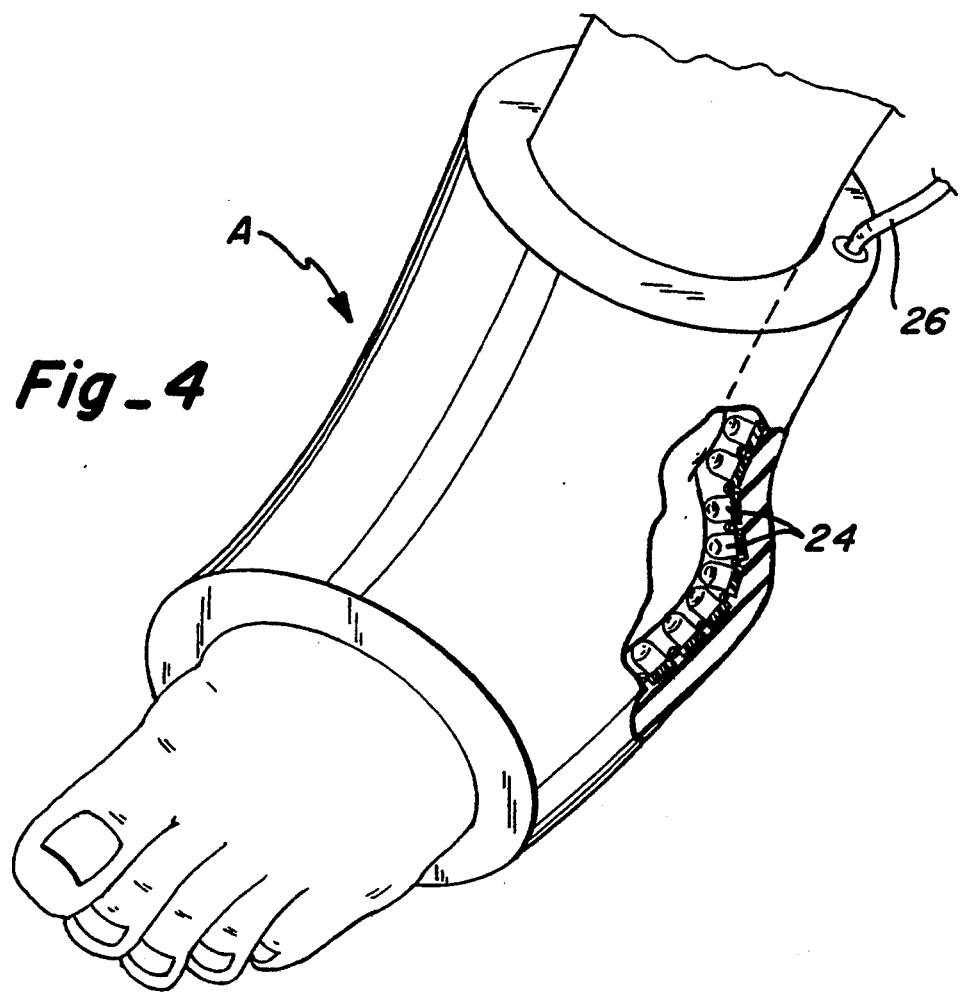
Fig_4

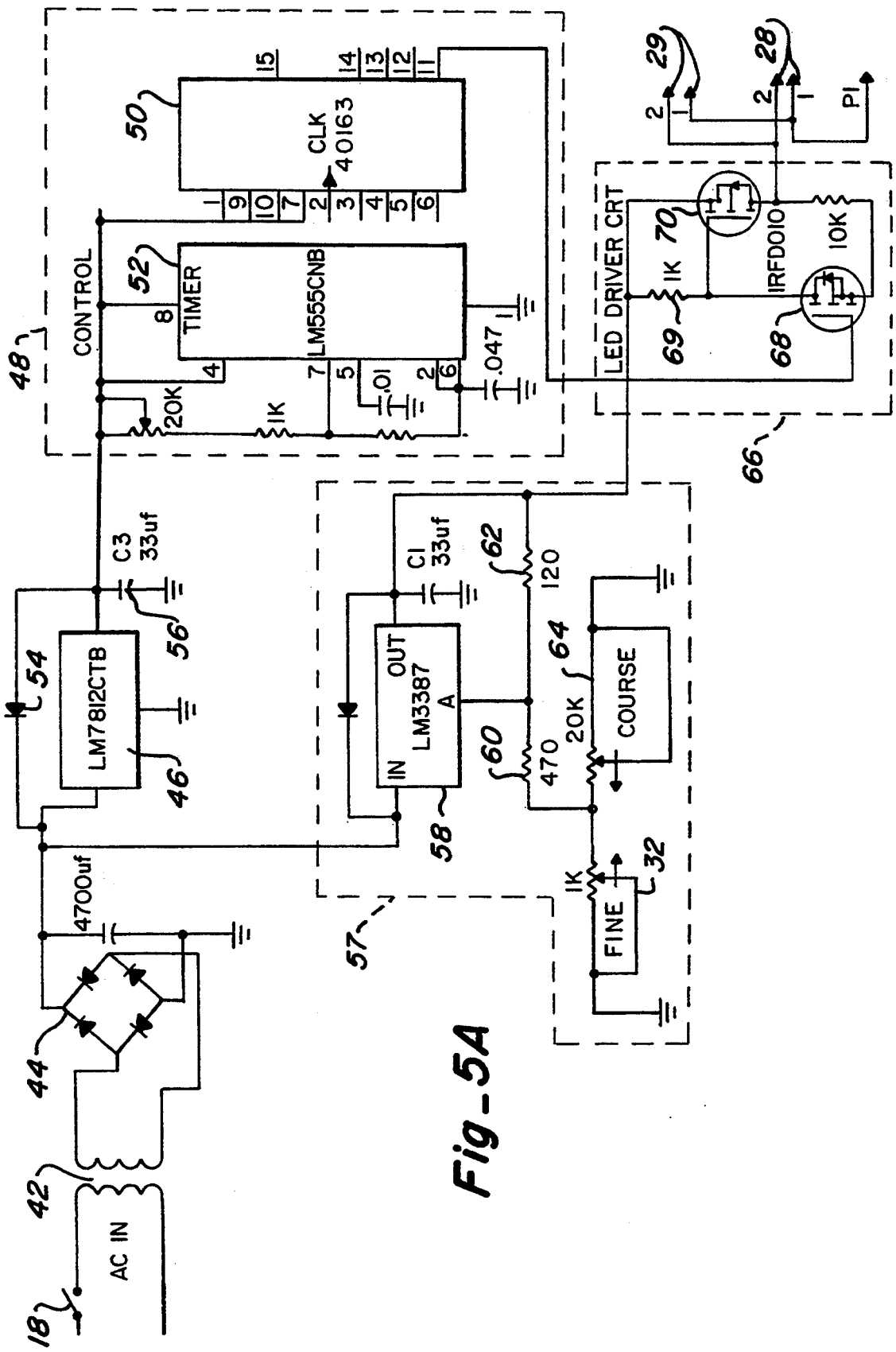
Fig_5A

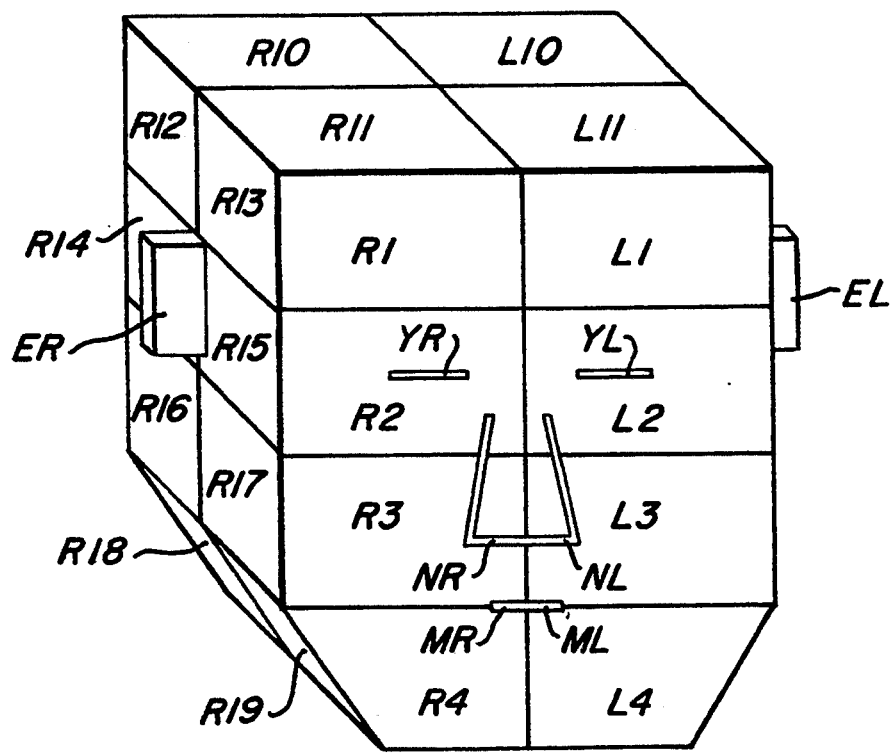
Fig_6

PHOTO-THERMAL THERAPEUTIC DEVICE AND METHOD

TECHNICAL FIELD

This invention relates to a photo-thermal therapeutic device and method wherein a plurality of photo diodes, projecting non-coherent light, are arranged in perpendicular contacting relationship to the skin of the patient to project cones of light in overlapping position and/or to serve as heat sinks to provide therapeutic heat through conduction from a heat source.

BACKGROUND ART

The benefits of using heat for treatment of muscular and joint pain is well-known. Also, the advantages of photo-therapy for the treatment of the same modalities as well as for the treatment of cuts and abrasions has been studied and certain implements for such treatment have been developed. Also, the treatment of muscular aches and pains through the use of heat is well known. However, to date no one has provided a method or apparatus which combines all of these modalities in an efficient and effective manner. In particular, no one has developed a therapeutic apparatus that provides accurate, uniform and consistent delivery of low level (non-lased, non-coherent) photo energy or optional simultaneous delivery of low level photo energy and therapeutic thermal energy. As used herein, therapeutic heat is heat in the range of 40 to 45 degrees centigrade.

U.S. Pat. No. 4,535,784 to Rohlicek et al discloses an apparatus for stimulating acupuncture points by light radiation in the visible light range or in the infrared range for medical purposes.

U.S. Pat. No. 5,024,236 to Shapiro discloses a photoprobe apparatus which includes an electric probe for locating acupuncture points and a light emitting diode to stimulate acupuncture points as well as injury sites. Only a single diode is used.

French Patent No. 2,591,902 discloses a device for treating arthritis in which a suction cup containing a plurality of pulsed laser light diodes is applied to the area of treatment. On a contoured surface the distance of the diodes from the skin surface will vary. Also, the photo energy will not be applied uniformly and consistently.

French Patent No. 2,371,935 discloses a device utilizing one pulsed infrared diode which provides treatment similar to acupuncture.

U.S. Pat. No. 3,900,034 to Katz et al. discloses the use of a laser photo diode for nerve stimulation which emits laser light in a range from infrared to ultraviolet. Visible light near the infrared range is preferred. Stain is used on the nerve to cause it to absorb the specific wavelength of light produced by the photo diode. The light is pulsed.

Soviet Union Patent No. 1,266,540 and Soviet Union Patent No. 1,289,493 each teach the use of multiple diodes positioned perpendicularly to the skin. In the '540 patent radiation is pulsed and is in the infrared range. A block of diodes in minihousings are secured with tape or plaster.

U.K. Patent No. 2,208,803 discloses a device for applying light to an acupuncture point wherein pulsed white light is projected through a filter of a desired color or through a thin slice of medicant.

U.S. Pat. No. 4,232,678 to Skovajsa discloses a device which utilizes an infrared diode with variable frequency for acupuncture and auriculotheraphy.

U.S. Pat. No. 4,597,380 to RAF et al. and U.S. Pat. No. 4,072,147 each disclose an endoscope which transmits laser light to an operative site within the body.

U.S. Pat. No. 4,583,526 to Ali and U.S. Pat. No. 4,604,992 to Sago shows devices similar to the above-mentioned RAF et al. patent.

U.S. Pat. No. 4,693,556 to McCaughan Jr.; U.S. Pat. No. 5,059,191 to Beer et al. and U.S. Pat. No. 4,998,930 each disclose devices which use red light conducted by optical fibers to an internal site in the human body to kill cancer cells or other tumors.

U.S. Pat. No. 5,009,655 to Diagnault, Jr. et al. discloses an optical device for angioplasty which heats the interior of an artery with an infrared light and treats the area with ultraviolet light.

The RESPOND LASER 2400 (not patented) provides four laser diodes which are mounted in a common head to project light through a red plastic shield. The treatment head is nonflexible, nonconforming and the laser light beams do not overlap for uniform coverage. Also, therapeutic heat is not available. The device is sold by Respond System, Inc. of Madison, Conn.

The BIOBEAM 660 is a device to provide photo energy for medical treatments. The treatment head is nonflexible and nonconforming. A recessed noncontacting light source projects through a lens nonuniform, noncoherent light to a small target zone (approximately 2 cm). The device is sold by Amcor LTD of Tel-Aviv, Isreal.

The BIOSCAN is a device to provide biosimultation to irritated tissues in horses. Similar to the BIOBEAM 660, the BIOSCAN treatment head is noncontacting, nonflexible, nonconforming and projects through a lens noncoherent, nonuniform light through a lens or shield to small target areas. This device is sold by Bioscan Incorporated, Corrales, N.M.

Each of these devices is satisfactory for its intended purpose. However, in most instances the use of each device is vary narrow and in some cases impractical for commercial application. None of the prior art references teach the combination of using a plurality of photo diodes which direct non-coherent light against the surface of the skin, wherein the diodes are flexibly mounted to conform to the treatment target or mounted in preconformed appliances which maintain diodes in a pattern substantially perpendicular to the surface of the skin, and in contact therewith for providing thermal as well as photo therapy simultaneously or selectively over a substantial area of treatment. Also, no one has devised a method for recording the nature of the malady being treated, the particular treatment applied and the results so that appropriate treatment can be repetitively supplied for particular medical complaints.

DISCLOSURE OF THE INVENTION

In accordance with this invention, an apparatus for photo-thermal treatment of an area of the skin and adjacent subcutaneous structure of a patient is provided. It includes a plurality of juxtaposed diodes defining a treatment area. Each diode has a longitudinal axis and is capable of projecting a non-coherent cone of light when energized. The cone of light from each diode overlaps the cone of light from each juxtaposed diode so that the light completely covers the treatment area. A means, such as flexible pad is provided for holding the diodes in juxtaposed position with each other. Each is held in contact with the skin and has a longitudinal axis which is in substantially perpendicular relationship to the skin. Means is provided for heating each diode so that the treatment area of the skin and the adjacent subcutaneous structure of the mammal receive light and thermal treatment simultaneously. Means is connected to the diodes and the heating means for activating each of them.

Preferably, the non-coherent light is in the red to infrared range. The activating means includes an adjustable control means for varying the light intensity of the diodes and the amount of light and thermal treatment simultaneously or selectively. The heating means includes a resistor and the control means includes a rheostat wherein the diodes act as a heat sink for absorbing the heat generated by each resistor for application to the treatment site by the diodes. This occurs through conduction because of the direct contact between the diodes and the skin in the treatment zone of the patient. The control means can also include indicia for visibly indicating the setting of the control means so that repetitive treatment is possible.

More specifically, the diodes are arranged in a plurality of rows, the diodes in each row being connected in series with each other and the rows being connected in parallel with each other. The heating means includes a resistor in each of the rows connected in series with the diodes in each row. The rows of diodes can be flexed with respect to each other so that each diode in each row of diodes can be held in substantially perpendicular relationship to the skin. The rows of diodes can be mounted in a single flexible pad or in a plurality of pads or in a preconformed appliance for simultaneous treatment of different areas of skin and adjacent subcutaneous structure.

The present invention contemplates a method of photo-thermal treatment of an area of the skin and subcutaneous structures adjacent to the area of the skin of a patient. The method includes placing a plurality of juxtaposed diodes in firm contact with the skin with the longitudinal axis of each diode in substantially perpendicular relationship with the skin. Each diode is caused to irradiate the skin and adjacent subcutaneous structure with overlapping cones of non-coherent light to completely cover a treatment area. Each diode may be heated so that it becomes a heat sink that conducts heat to the skin and adjacent subcutaneous structure at the same time the skin and the adjacent subcutaneous structure is irradiated with the overlapping cones of light. These steps can be performed simultaneously on a plurality of skin areas and adjacent subcutaneous structures.

The method includes the further step of recording information concerning the specific body area of the patient being treated and the results of such treatment. To accomplish this, a target grid system is overlaid on the skin or target surface of the patient to separate it into predetermined areas which can be subjected to treatment in accordance with this invention. The treatment undertaken and the results obtained can be recorded. By providing such treatment to a population of patients for a variety of needs, the information can be recorded concerning specific body areas of each patient treated and the results of such treatment. This tabulated information can be used to determine which body areas provide the most desirable response to treatment for specific needs. Utilizing the tabulated information, a specific treatment can be designed for another patient with a similar predetermined need.

Although the present invention is intended primarily for use on mammals, it can also be effective when used on birds, reptiles, fish and other living organisms.

BRIEF DESCRIPTION OF THE DRAWINGS

FIG. 1 is a perspective view of a photo-thermal therapeutic device constructed in accordance with this invention;

FIG. 2 is a fragmentary, enlarged plan view of a pad of the device of FIG. 1 showing the overlapping cones of light;

FIG. 3 is a perspective view showing the application of a pad of FIGS. 1 and 2 to the skin of a patient with each diode held perpendicularly to the surface of the skin;

FIG. 4 is a fragmentary perspective view showing an appliance for use with the apparatus of FIG. 1;

FIG. 5A is a circuit diagram of the circuitry for control of the pad;

FIG. 6 is a perspective view of one form of a grid system for use on the head of a human.

BEST MODE FOR CARRYING OUT THE INVENTION

Figure 5B:
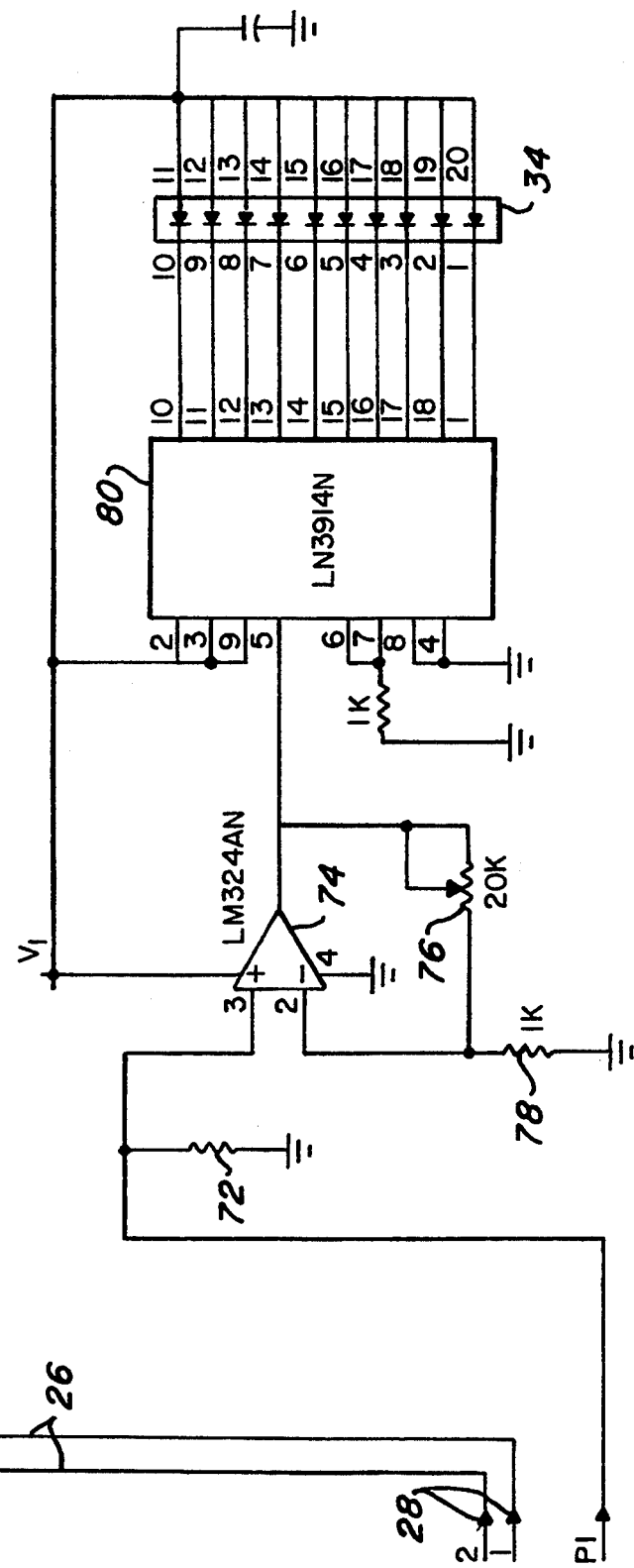
FIG. 5B is a circuit diagram of the pad and the visual display for the apparatus of FIG. 1.

In accordance with this invention, a photo-thermal device D is provided as shown in FIG. 1 which includes a housing for housing the circuitry of FIG. 5A and a portion of the circuitry of FIG. 5B, as more fully explained below. Conveniently, the housing comprises opposite side walls 10 and 12, interconnected by a top cover 14 and having a face plate 16. A switch 18 is provided on cover 14 for selectively supplying electrical power to the circuitry to FIGS. 5A and 5B, as through power cord 20. A pair of pads P each comprise a flexible pad housing 22 in which an array of photo diodes 24 are mounted for supplying non-coherent light, in a manner to be described. Power to the diodes is supplied through wires 26 which are connected by means of jacks 28 to the circuitry of Figure a through face plate 16. The amount of current supplied to pads P is controlled by a knob 30 connected to rheostat 32 of FIG. 5A. A light bar display 34 provides visual indicia for determining the amount of current supplied to the pads P.

As best seen in FIG. 5B, the diodes 24 are arranged in a plurality of rows which are connected in parallel with each other and each row has a resistor connected in series with each row of diodes 24. The diodes 24 act as heat sinks in that they absorb heat from each of their respective resistors. Thus, the diodes can provide heat therapy and photo-therapy simultaneously. If desired, a separate resistor can be provided for each diode, as will be apparent to one skilled in the art. As best seen in FIG. 3, the rows of diodes flex with respect to each adjacent row within pad 22 so that the longitudinal axis, such as axis 38 of the diodes 24 is perpendicular to the surface of the skin. Thus, each diode projects a cone of light 40 wherein the cones of lights of the juxtaposed diodes 24 overlap each other to provide complete coverage of a treatment area covered by the diodes of pad P. In this way, the entire treatment area receives both photo and thermal treatment simultaneously or selectively to provide the greatest benefit to the patient.

An alternative embodiment is shown in FIG. 4 wherein the diodes are formed in an appliance A which may be in the form of an elastic sleeve to slip over a limb or other portion of a body to be treated and is connected by means of a wire 26' to photo-thermal device D. Conveniently, this appliance holds each of the diodes perpendicular with the skin of the patient for most effective treatment, as previously discussed. Although the device shown in FIG. 4 is for an ankle, it will be understood that anatomically specific appliances can be preformed or specifically tailored to accommodate any target, such as an ankle, elbow, wrist, knee, hand, foot, shoulder, hip, neck, lumbar area, etc. The appliance can be made of any appropriate material. The diodes can be independently mounted or mounted in strips, as illustrated in the drawings.

Turning to FIG. 5A, it can be seen as switch 18 closes the circuit from a AC voltage source which is rectified by bridge 42 to convert 110 volt line voltage to 6.0 volts. This AC voltage is rectified by bridge 44 and is converted to a 12 volt DC voltage by regulator 46. The voltage regulator supplies control circuit 48 that includes a binary counter 50 which is used as a frequency divider to generate frequencies of 18, 688, 9344, 4672, 2336, 1168, 584 and 292 Hz at a 50% duty cycle. The binary counter is controlled by a timer 52. Diode 54 protects voltage regulator 46 from capacitor 56. A variable voltage regulator circuit 57 includes a voltage regulator 58, resistors 60 and 62 and a potentiometer or rheostat 32 for fine adjustment by knob 30 of FIG. 1 which can vary the voltage from approximately 6.5 to 15.0 volts. A potentiometer 64 is provided which is used for course adjustment within photo-therapeutic device D at the time of manufacture. Potentiometer 64 is accessible only from the inside of the housing of device D by a technician and not by the purchaser of the device. Potentiometer 64 is used to set the maximum output voltage of regulator circuit 57.

Voltage regulator circuit 57 is connected to driver circuit 66 which includes transistor 68 in series with resistor 69 and transistor 70. Transistor 68 and resistor 69 function as a voltage level shifter. When the output of the frequency divider 50 is low (approximately 0 volts), the voltage on the drain of transistor 68 will be the same as the output of the voltage regulator 46, thus prohibiting the flow of current through transistor 70 and the diode pad P. When the output of the frequency divider is 12 volts, the voltage on the drain of transistor 68 is approximately 0 volts which will turn on transistor 70 and allow current to flow through transistor 70 and diode pad P. Voltage regulator 46 controls voltage to frequency divider 50. Transistor 70 provides current to jacks 28 and 29 through their respective pins 1 and 2.

$$I = (V - 5 \times F)/R$$

Where I is the current through each diode 24, V is the output of the voltage regulator circuit and F is the forward biased voltage of the LADS and R is the effective value of the parallel resistors.

As shown in FIG. 5B, the pad consists of a plurality of rows of diodes 24 which project non-coherent light, each row being connected in series with a resistor 36 to provide heat to the diodes. Thus, by turning knob 30 of potentiometer 32 in one direction, the current to the photo diodes 24 is increased thereby increasing the amount of light and the amount of heat transferred to the skin of the patient.

The LED bar graph circuit for light bar display 34 is shown in FIG. 5B and is supplied with power through pin P. The current used to light the photo diodes is returned from the photo diode pad through resistor 72, thus converting the current to a voltage. Amplifier 74 and potentiometer 76 and resistor 78 are wired as a non-inverting amplifier with a gain of approximately 10 which is used to amplify the voltage across resistor 72. The gain can be varied by adjusting the C potentiometer 76. The gain can be calculated by using the following equation:

$$GAIN = 1 + (R3/R4)$$

The amplified voltage is connected to bar graph driver 80, which consists of 10 voltage comparisons. All of the photo diodes on bar graph 34 will be lighted when the signal on pin 5 of bar graph driver 80 is greater than or equal to 1.25 volts.

The invention also contemplates a method of providing preselected treatment for the specific needs of a patient to be treated by mapping the skin area of the patient into different regions for receiving treatment. The method contemplates providing treatment in response to specific needs and recording the results of these treatments in various areas of the mapped portion of the patients for providing a database by which future treatment of additional patients can be made based on a population of patients who have previously had their skin mapped and whose treatment and the results of treatment have been recorded and tabulated. This mapping involves developing a grid system over the entire body surface of the patient, as shown in FIG. 6. FIG. 6 is limited to the head of the patient and is specific for a human patient. However, the same technique could be applied to all body areas of a patient and the patient may be a patient other than a human. This is accomplished by providing unique nomenclature for each area of the grid system, as shown in FIG. 6, and correlating the nomenclature for each area with the effective treatment for the patient based on the tabulated information. Thus patients may be of the same species, the same sex and/or may be human.

This invention has been described in detail with reference to particular embodiments thereof, but it will be understood that various other modifications can be effected within the spirit and scope of this invention.

I claim:

1. Apparatus for simultaneous treatment of an area of the skin and adjacent subcutaneous structures of a patient utilizing photo energy and therapeutic thermal energy, said apparatus comprising:

a plurality of juxtaposed diodes, defining a treatment area, each diode having a longitudinal axis and being capable of projecting a non-coherent cone of light when energized, the cone of light from each diode overlapping the cone of light from each other juxtaposed diodes so that the light completely covers the treatment area;

means for holding each of said diodes in juxtaposed position with each other and in contact with the skin in substantially perpendicular relationship to said longitudinal axis;

means for heating each of said diodes so that the treatment area of the skin and the adjacent subcutaneous structure of the patient receive light treatment and thermal treatment simultaneously or selectively; and means connected to said diodes and said heating means for activating each of them.

2. Apparatus as claimed in claim 1, wherein:
said non-coherent light is in the red to infrared range.

3. Apparatus, as claimed in claim 1, wherein said activating means includes:
adjustable control means for varying at least one of the light intensity of said diodes and the amount of heat generated by said heating means.

4. Apparatus, as claimed in claim 1, wherein: said activating means includes:
adjustable control means for varying both the light intensity of said diodes and the amount of heat generated by said heating means.

5. Apparatus, as claimed in claim 1, wherein:
said holding means includes a flexible pad in which said diodes are mounted for holding said diodes in said perpendicular relationship.

6. Apparatus, as claimed in claim 1, wherein:
said holding means includes an appliance for holding said diodes in a predetermined fixed position with respect to the skin of the patient 7. Apparatus, as claimed in claim 6, wherein:
said appliance is an elastic sleeve.

8. Apparatus, as claimed in claim 6, wherein:
said apparatus is a preconformed appliance.

9. Apparatus, as claimed in claim 1, wherein:
said heating means includes at least one resistor; and said control means includes a rheostat.

10. Apparatus, as claimed in claim 3, wherein:
said control means includes indicia for visually indicating the adjustment of said control means.

11. Apparatus, as claimed in claim 1, wherein:
said diodes are arranged in a plurality of rows, the diodes in each row being connected in series and said rows being connected in parallel; and
said heating means includes a resistor in each said row connected in series with said diodes in each said row.

12. Apparatus, as claimed in claim 11, wherein:
said rows of diodes can be flexed with respect to each other so that each row of diodes can be held in substantially perpendicular relationship to the skin.

13. Apparatus, as claimed in claim 12, wherein:
said rows of diodes are mounted in a pliable pad.

14. Apparatus, as claimed in claim 13, wherein:
said rows of diodes are mounted in a plurality of pliable pads for simultaneous treatment of different areas of skin and adjacent subcutaneous structures.

15. A method of photo-thermal treatment of an area of the skin and subcutaneous structures adjacent the area of the skin of a patient, said method comprising the steps of:
placing a plurality of juxtaposed diodes, each of which has a longitudinal axis, in firm contact with the skin with the axis of each diode in substantially perpendicular relationship with the skin;
causing each of the diodes to irradiate the skin and adjacent subcutaneous structure with overlapping cones of non-coherent light to completely cover a treatment area; and
heating each of the diode so that each diode becomes a heat sink that conducts therapeutic heat to the skin and adjacent subcutaneous structure at the same time the skin and adjacent subcutaneous structure is irradiated with the overlapping cones of light.

16. A method, as claimed in claim 15, further including:
simultaneously performing the steps of claim on a plurality of skin areas and the adjacent subcutaneous structures of each skin area respectively.

17. A method, as claimed in claim 15, including the further step of:
holding the diodes in firm contact with the skin by use of an appliance.

18. A method, as claimed in claim 15, including the further step of:
recording information concerning the specific body area of the patient being treated and the results of such treatment.

19. A method, as claimed in claim 18, including the further step of:
using the recorded information for determining future treatment for specific needs of the patient to be treated.

20. A method of determining a desirable photo-thermal treatment for the needs of a patient, said method comprising:
providing a grid system over at least a portion of the body surface of the patient to be treated wherein each area in the grid system represents a particular skin area on the patient;
providing unique nomenclature for each area in the grid system;
providing treatment to a population of patients for a variety of needs in accordance with the steps set forth in claim 14;
recording information concerning the specific body area of each patient treated and the results of each treatment;
tabulating the information to determine the body areas which provide the most desirable response to treatment for specific needs; and
correlating the nomenclature for each area with effective treatment for the patient based on the tabulated information.

21. A method, as claimed in claim 20, wherein:
each patient is of the same species.

22. A method, as claimed in claim 20, wherein:
each patient is of the same sex.

23. A method, as claimed in claim 20, wherein:
each patient is human.

* * * * *